United States Patent [19]

Trumble

[11] Patent Number: 5,479,946
[45] Date of Patent: Jan. 2, 1996

[54] MUSCLE ENERGY CONVERTER

[75] Inventor: Dennis R. Trumble, Pittsburgh, Pa.

[73] Assignee: Allegheny-Singer Research Institute, Pittsburgh, Pa.

[21] Appl. No.: 228,586

[22] Filed: Apr. 15, 1994

[51] Int. Cl.$^6$ .................................................. A61M 1/12
[52] U.S. Cl. ............................................. 128/899; 600/16
[58] Field of Search ................................. 128/897, 898, 128/899; 600/16; 623/3, 26

[56] References Cited

U.S. PATENT DOCUMENTS

| | | | |
|---|---|---|---|
| 3,614,181 | 10/1971 | Meeks . | |
| 5,055,005 | 10/1991 | Kletschka | 600/16 |
| 5,147,281 | 9/1992 | Thornton et al. | 600/16 |
| 5,344,385 | 9/1994 | Bock et al. | 600/16 |

OTHER PUBLICATIONS

"A New Skeletal Linear–pull Energy Convertor as a Power Source for Prosthetic Circulatory Support Devices", David J. Farrar, Ph.D. and J. Donald Hill, M.D., *The Journal of Heart and Lung Transplantation*, vol. 11, No. 5, Sep./Oct. 1992, pp. S341–S350.

"A Skeletal Muscle Actuator for an Artificial Heart", Sasaki et al., ASAIO Journal 1992, pp. M507–M511.

"Implantable Rate–Responsive Counterpulsation Assist System", Li et al., Ann Thorac Surg, 1990; 49:356–62.

"Muscle Powered Circulatory Assist Device for Diastolic Couterpulsator", Novoa et al., vol. XXXV, *Trans Am Soc Artif Intern Organs*, 1989, pp. 408–411.

"Long–Term Neurostimulation of Skeletal Muscle: Its Potential for a Tether–Free Biologic Cardiac Assist Device", Anderson et al., *PACE*, vol. 11, Nov. 1988, Part II, pp. 2128–2134.

"The Muscle–Powered Dual–Chamber Counterpulsator: Rheologically Superior Implantable Cardiac Assist Device", Kochamba et al., *Ann Thorac Surg*, 45:620–625, Jun. 1988.

"An Implantable Power Source for an Artificial Heart or Left Ventricular Assist Device", D. Spitzer, vol. XXXI, *Trans Am Soc Artif Intern Organs*, 1985, pp. 193–195.

"A Small Ventricle–Type Pump for Prolonged Perfusions: Construction and Initial Studies, Including Attempts to Power a Pump Biologically with Skeletal Muscle", Kusserow et al., vol. X, *Trans. Amer. Soc. Artif. Int. Organs*, 1964, pp. 74–78.

*Primary Examiner*—William E. Kamm
*Attorney, Agent, or Firm*—Ansel M. Schwartz

[57] ABSTRACT

A muscle energy converter comprised of a piston having an attachment head for connection to a muscle. The muscle energy converter also comprises a cylinder having a chamber in which the piston is disposed. The cylinder has a port for transport of fluid in the chamber as the muscle moves the piston. Preferably, movement of the piston within the cylinder is frictionless. The piston comprises a first magnetic section and the cylinder comprises a second magnetic section. The first magnetic section and the second magnetic section provide opposing fields to maintain the piston in co-axial alignment within the cylinder. Preferably, there is a rolling diaphragm sealing mechanism connected between the piston and the cylinder. The rolling diaphragm mechanism can include a first rolling diaphragm and a second rolling diaphragm spaced from and opposing the first rolling diaphragm. Preferably, the opposing fields of the first magnetic section and the second magnetic section are disposed at an angle between the axial and radial direction of the piston so as the piston is subject to both a radial aligning force and an axial preload force. The present invention is also a method of using muscle energy. The method comprises the steps of attaching a muscle to an attachment head of a piston so that the muscle can move the piston within a cylinder to pressurize fluid within the cylinder. Then there is the step of maintaining frictionless alignment of the piston within the cylinder with opposing magnetic fields produced by first and second magnetic sections in the piston and cylinder, respectively. Preferably, there is the step of producing with the first and second magnetic sections a preload force on the piston. Preferably, after the attaching step, there is the step of using the fluid to perform work within the human body such as to pump blood.

17 Claims, 7 Drawing Sheets

MUSCLE ENERGY CONVERTER

CROSS-REFERENCE

This application is related to contemporaneously filed U.S. patent application Ser. No. 08/228,150, titled "Occluder Device and Method of Making", by John J. Pacella and Richard E. Clark, having attorney docket number AHS-3, incorporated by reference herein; and is related to contemporaneously filed U.S. patent application Ser. No. 08/228,433, titled "Blood Pump Device and Method of Producing", by John J. Pacella, Andrew H. Goldstein, Dennis R. Trumble, Richard E. Clark and Fred W. Moeller, having attorney docket number AHS-4, incorporated by reference herein.

1. Field of the Invention

The present invention is related to medical devices. More specifically, the present invention is related to a device for converting muscle power into alternative forms of body work.

2. Background of the Invention

The idea of using endogenous skeletal muscle as an energy source for cardiac assistance is not new. Many investigators have demonstrated that untrained skeletal muscle can provide circulatory support for short periods of time (minutes to hours). However, early studies were plagued by rapid muscle fatigue which discouraged the use of skeletal muscle as a long-term energy source for biomechanical assistance. This ultimately prompted researchers to explore the possibility of conditioning skeletal muscle via chronic electrical stimulation.

The ultimate objective of chronic myostimulation is to transform muscle to a fatigue-resistant state so that it performs much like the myocardium, which is an oxidative muscle capable of continuously pumping blood. Both cardiac and skeletal muscle contain contractile proteins which transform chemical energy into mechanical work, but skeletal muscle comprises several types of muscle cells with different physiologic and metabolic characteristics. These contractile fibers may be either glycolytic (fatigue-susceptible) or oxidative (fatigue-resistant). Slow-twitch muscle is generally oxidative, while more powerful fast-twitch muscle can be either glycolytic or oxidative. In order to utilize skeletal muscle for long-term circulatory assist, a conditioning scheme is needed to convert these fibers from glycolytic to oxidative metabolism.

The feasibility of converting fast-twitch muscle fibers to fatigue-resistant slow-twitch fibers was demonstrated by Salmons and Sreter in the mid-70s. (Salmons, S., and Sreter, F. Significance of impulse activity in the transformation of skeletal muscle type. Nature, vol. 263, 30–34, 1976). Since then, interest in skeletal muscle conditioning has increased and has become a major subject of current studies. (Sreter, F., Pinter, K., Jolesz, F., and Mabuchi, K., Fast to slow transformation of fast muscles in response to long-term phasic stimulation. Experimental Neurology, vol. 75, 95–102, 1982; Macoviak, J., Stephenson, L., Armenti, F., Kelly, A., Alavi, A., Mackler, T., Cox, J., Palatianos, G., and Edmunds, L., Electrical conditioning of in situ skeletal muscle for replacement of myocardium. J. Surgical Research, vol. 32, 429–439, 1982). Recently, both Frey and Dewar have shown that a short train or "burst" of pulses is effective in producing a sustained contraction with complete conversion of skeletal muscle to fatigue-resistant fibers. (Frey, M., Thoma, H., Gruber, H., Stohr, H., Huber, L., Havel, M., and Steiner, E. The chronically stimulated muscle as an energy source for artificial organs. Eur. Surgical Research, vol. 16, 232–237, 1984; Dewar, M., and Chiu, R. Cardiomyoplasty and the pulse-train stimulator. Biomechanical Cardiac Assist, Futura Publ. Co., 43–58, 1986).

This knowledge has led to a myriad of new techniques designed to utilize the transposition of conditioned contractile tissue. Applications include cardiomyoplasty, diastolic counterpulsation, and using the muscle as an energy source to drive cardiac assist devices. To date, most attempts to harvest this new power source have involved wrapping a muscle flap around the heart, aorta or prosthetic conduit, or shaping the muscle into a neo-ventricle. (Magovern, G., Park, S., Kao, R., Christlieb, I., and Magovern, Jr., G. Dynamic cardiomyoplasty in patients. J. Heart Transplantation, vol. 9, 258–263, 1990; Pattison, C., Cumming, D., Williamson, A., Clayton-Jones, D., Dunn, M., Goldspink, G., and Yacoub, M. Aortic counterpulsation for up to 28 days with autologous latissimus dorsi in sheep. J. Thoracic Cardiovascular Surgery, vol. 102, 766–773, 1991; Mannion, J., Hammond, R., and Stephenson, L. Hydraulic pouches of canine latissimus dorsi; potential for left ventricular assistance. J. Thoracic Cardiovascular Surgery, vol. 91, 534–544, 1986; Hammond, R., Bridges, C., DiMeo, F., and Stephenson, L. Performance of skeletal muscle ventricles: effects of ventricular chamber size. J. Heart Transplantation, vol. 9, 252–257, 1990).

These efforts have met with only limited success because of insufficient power generation, slow relaxation, muscle atrophy, and thromboembolism. Wrapping the muscle flap is an inefficient means for collecting muscle energy and requires complete mobilization of the muscle, which interrupts some of its blood supply and increases the development of fibrosis. It is apparent that muscle-wrapping techniques are not the best way to harvest useful work from skeletal muscle, and that alternative pumping schemes should be explored.

Previous studies have demonstrated that certain large skeletal muscles can produce high amounts of aerobic (steady-state) energy if the muscle is left in situ and allowed to contract linearly. For example, Ugolini recently published an article describing an energetic balance of the human psoas major that predicts a steady-state power capacity of 5.19 watts. (Ugolini, F. Skeletal muscle for artificial heart drive: theory and in vivo experiments. Biomechanical Cardiac Assist, Futura Publ. Co., 193–210, 1986). This power level would be more than sufficient to drive a hydraulic artificial heart (which has a typical power requirement of <1.2 watts) if a means could be devised to efficiently convert this energy into pumping power.

Logically, one of the most effective ways to harness muscular work for this purpose would be to employ a linear arrangement with the muscle tendon detached from its original insertion point and reconnected to a hydraulic energy converter. This hypothesis has recently been tested by Sakakibara (Sakakibara, N., Tedoriya, T., Takemura, H., Kawasuji, M., Misaki, T., and Watanabe, Y. Linear muscle contraction for actuation of a muscle-powered cardiac assist device (MCAD): an ex vivo pilot study. ASAIO Abstracts, vol. 21, p. 53, 1992), who evaluated the performance of latissimus dorsi (LD) muscle in three orientations: roll (wrap) type; compressive type; and linear type. This study showed that linear actuation produced a six-fold improvement in work output versus wrap-type, and a 50% increase over the compressive arrangement.

Another study, performed by Geddes at Purdue University (Geddes, L., Badylak, S., Tacker, W., and Janas, W. Output power and metabolic input power of skeletal muscle contracting linearly to compress a pouch in a mock circulatory system. J. Thoracic and Cardiovascular Surgery, vol. 104, 1435–1442, 1992), utilized three different groups of muscles (contracting linearly) to compress a valved pouch in a hydraulic model of the circulation. Output power and metabolic input power were measured at contraction rates from 10 to 40 per minute. Muscle blood flow increased dramatically during periods of work, and fatigue was not a factor even though unconditioned muscles were used. Continuous power generation of over 2 watts was recorded for all groups, with an energy conversion efficiency approximating that of cardiac muscle (10%). Based on these data, Geddes concluded that an energy-conversation scheme should be sought in which linear shortening of skeletal muscle could be used to assist the circulation.

The concept of powering a pump with linearly contracting muscle appeared in the literature as early as 1964, when Kusserow and Clapp employed a quadriceps femoris muscle to drive a spring-loaded diaphragm pump. (Kusserow, B., and Clapp, J. A small ventricle-type pump for prolonged perfusions: construction and initial studies, including attempts to power a pump biologically with skeletal muscle. Trans. ASAIO, vol. 10, 74–78, 1964.) Since that time, a number of investigators have addressed this topic, yet no serious attempts to develop such a device were published until Sasaki in 1992. (Sasaki, E., Hirose, H., Murakawa, S., Mori, Y., Yamada, T., Itoh, H., Ishikawa, M., Senga, S., Sakai, S., Katagiri, Y., Hashimoto, M., Fuwa, S., and Azuma, K. A skeletal muscle actuator for an artificial heart. ASAIO Journal, vol. 38, 507–511, 1992.) His system employs a flexible rod, sheath, crank, and cam to transmit muscle power to a pusher-plate pump. This scheme was tested in dogs using an untrained latissimus dorsi muscle and a mock circulatory system. At 60 beats per minute, this device maintained 0.8–2.0 L/min for 200 minutes against an afterload of 75 mmHg. Output power was 2.5 mW/gram, and system efficiency approached 50%.

Most recently, Farrar and Hill developed a new muscle-powered, linear-pull energy converter for powering various implantable devices. (Farrar, D., and Hill, J. A new skeletal linear-pull energy convertor as a power source for prosthetic circulatory support devices. J. Heart and Lung Transplantation, vol. 11, 341–350, 1992.) This device consists of a metal cylinder which houses a piston-type actuator to which the muscle is attached. As the muscle contracts, up to 2 ml of hydraulic fluid is displaced into a transmission line leading to the blood pump. During relaxation, a spring is employed to assist pump filling and muscle lengthening. This device has problems, though. For instance, energy convertor components were purchased off the shelf, and no attempt was made to minimize energy losses. Consequently, the efficiency of this device was found to be only 22.5%.

Clearly, interest in muscle-powered assist devices is on the rise. However, efforts to date have produced systems that employ conventional mechanisms subject to frictional losses and component wear. Not only does this limit the lifetime of the prosthesis, but reduces the amount of work obtained from the muscle. Given the limited aerobic capacity of skeletal muscle, future research must focus on optimizing system efficiency in order to ensure long-term operation and effective muscle use.

SUMMARY OF THE INVENTION

The present invention is comprised of a muscle energy converter. The muscle energy converter is comprised of a piston having an attachment head for connection to a muscle. The muscle energy converter also comprises a cylinder having a chamber in which the piston is disposed. The cylinder has a port for transport of fluid in the chamber as the muscle moves the piston. Preferably, movement of the piston within the cylinder is frictionless.

The piston comprises a first magnetic section and the cylinder comprises a second magnetic section. The first magnetic section and the second magnetic section provide opposing fields to maintain the piston in proper alignment within the cylinder. Preferably, there is a rolling diaphragm sealing mechanism connected between the piston and the cylinder. The rolling diaphragm mechanism can include a first rolling diaphragm and a second rolling diaphragm spaced from and opposing the first rolling diaphragm. Preferably, the opposing fields of the first magnetic section and the second magnetic section are disposed at an angle between the axial and radial direction of the piston so that the piston is subject to both a radial aligning force and an axial preload force. For instance, the first magnetic section and the second magnetic section can have a series of ridged edges forming flat angled surfaces from which the opposing magnetic fields are emitted at an angle between the axial and radial directions. There can be nonmagnetic cover material disposed over the ridged edges to form a smooth outer surface.

The muscle energy converter preferably comprises a piston stroke regulation mechanism. The stroke regulation mechanism preferably comprises a central ring magnet fixedly connected to the piston which oppose first and second spaced portions of the second magnetic section. The ring magnet is disposed in a space between the first and second portions for providing travel. The cylinder can also comprise mounting hardware for attaching to bones in a body.

The present invention is also a method of using muscle energy. The method comprises the steps of attaching a muscle to an attachment head of a piston so that the muscle can move the piston within a cylinder to pressurize fluid within the cylinder. Then there is the step of maintaining frictionless alignment of the piston within the cylinder with opposing magnetic fields produced by first and second magnetic sections in the piston and cylinder, respectively. Preferably, there is the step of producing with the first and second magnetic sections a preload force on the piston. Preferably, after the attaching step, there is the step of using the fluid to perform work within the human body such as to pump blood.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1:
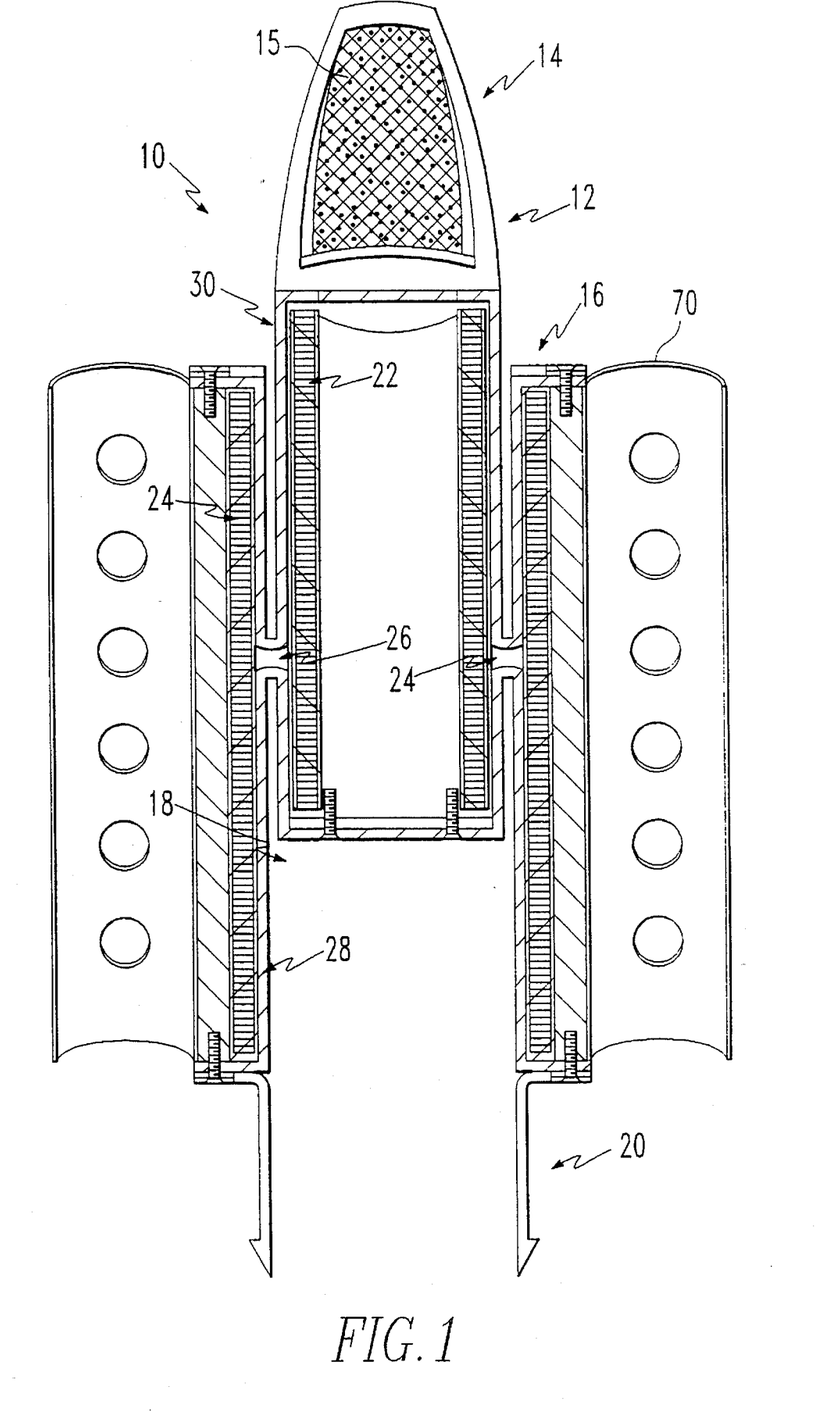
FIG. 1 is a schematic representation showing the muscle energy converter.

Referring now to the drawings wherein like reference numerals refer to similar or identical parts throughout the several views, and more specifically to FIG. 1 thereof, there is shown a muscle energy converter 10. The muscle energy converter 10 comprises a piston 12 having an attachment head 14 for connection to a muscle 13. The muscle energy converter 10 also comprises a cylinder 16 having a chamber 18 in which the piston 12 is disposed. The cylinder 16 has a port 20 for transport of fluid in the chamber 18 as the muscle moves the piston 12. Preferably, movement of the piston 12 within the cylinder 16 is frictionless. In order to maintain frictionless alignment of the piston 12 within the cylinder 16, the piston 12 comprises a first magnetic section 22 about the piston 12 and the cylinder 16 comprises a second magnetic section 24. The first magnetic section 22 and the second magnetic section 24 are disposed adjacent to each other and provide opposing fields to maintain the piston 12 in proper alignment within the cylinder 16. There can also be included a rolling diaphragm sealing mechanism 26 connected between the piston 12 and the cylinder 16. The rolling diaphragm mechanism 26 can comprise a first rolling diaphragm 28 and a second rolling diaphragm 30 spaced from and opposing the first rolling diaphragm 28.

Figure 2B:
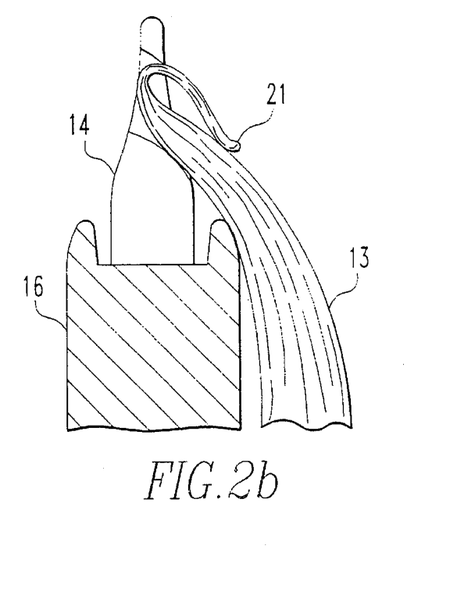
Figure 3:
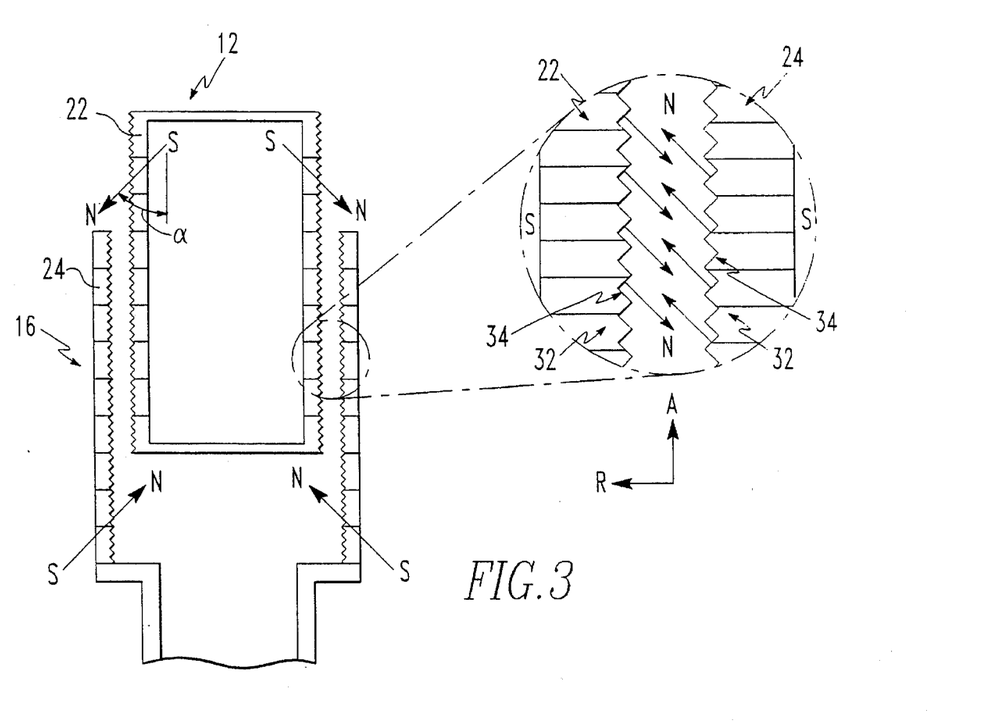
FIG. 3 is a schematic representation showing angled ridged edges of the magnetic sections and associated angled opposing magnetic field lines.

As shown in FIG. 3, the piston 12 moves relative to the cylinder 16 in an axial direction, A, perpendicular to a radial direction R. Preferably, the opposing fields of the first magnetic section and the second magnetic section 24 are disposed at an angle, α, between the axial and radial directions, relative to the axial direction, A, so as the piston 12 is subject to both a radial aligning force and an axial preload force by the angled opposing magnetic fields. It should be appreciated overcoming alignment problems between the piston 12 and cylinder wall 16 allows the muscle to be effectively attached as shown in FIG. 2b. Anatomically, the muscle is attached to the side of the piston surface 15. Therefore, muscle movement will impart not only a downward axial force, but a force in the radial direction as well, causing the piston 12 to tilt inside the cylinder 16 and make contact therewith. The present invention overcomes this tilting problem.

A secure attachment between the muscle tendon and piston is critical. Clearly, muscle power cannot be harnessed long-term unless this physical connection is maintained. One design includes a sewing patch as depicted in FIG. 1. The tendon can be sutured directly to this material, such as Dacron® or Gortex®, so that the tendon covers the patch and muscle shortening moves the piston 12 into the cylinder 16.

Figure 2A:
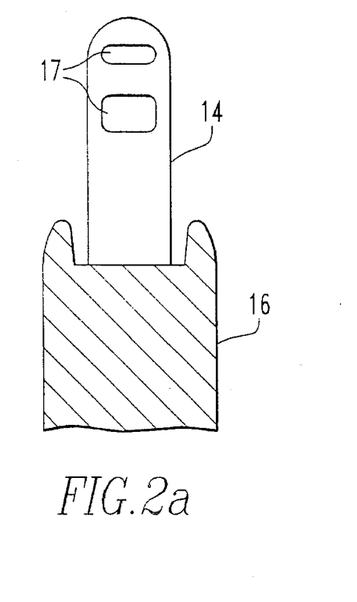
FIGS. 2a and 2b are schematic representations showing a muscle energy converter having an attachment head with slots for connection to a tendon.

As shown in FIG. 2a, in order to form a strong, reliable connection to the muscle 13, the attachment head 14 can have slots 17 machined through the head 14. These slots allow the tendon 21 of the muscle 13 to be pulled through and sutured back onto itself as shown in FIG. 2b. The slots 17 can be shaped and curved to automatically support the tendon 21. This design eliminates the tendon/patch interface and relies on a tendon-to-tendon anchor point which is very strong and stable.

By embedding magnetic sections 22 and 24 along the outside of the piston 12 and along the inside of the cylinder 16, respectively, the repulsive forces are utilized to maintain proper alignment despite the radial force provided by the muscle 13. Moreover, the magnetic sections 22, 24 and rolling diaphragm mechanism 26 combine to produce a muscle-powered pump with essentially no mechanical friction, making the described muscle energy converter 10 highly efficient.

A rolling diaphragm mechanism 26 requires two fundamental conditions in order to maintain nominal operation, parallel alignment of the piston 12 with respect to the cylinder 16 and a clear spacing between the cylinder 16 and piston 12. The first condition is maintained by the first and second magnetic sections 22 and 24. The second condition is preserved in vivo via the use of a second rolling diaphragm 30 inverted over the first 28, as illustrated in FIG. 1.

The second (external) rolling diaphragm 30 serves to keep the first rolling diaphragm 28 free from biological debris, so that it will continue to roll smoothly. Without this protection, blood products would likely build up between the first rolling diaphragm 28 and the walls of the piston and cylinder, causing the rolling diaphragm 28 to contact itself and eventually foul.

The second external rolling diaphragm 30 can be made an integral part of an outer coating which envelopes the entire pump 10. The action of the piston 12 during the up-stroke (i.e. diastole) serves to expel any foreign matter trapped within the convolution of the external rolling diaphragm 30, thereby keeping the first rolling diaphragm 28 clean.

It is desirable to have a preload force against the piston 12 to provide balance with the muscle (i.e. to pull the muscle back to length). To eliminate any springs in the device, the configuration of the magnetic sections 22 and 24 is preferably designed so that the opposing fields approach one another at an angle, α, rather than perpendicular to the side walls, as shown in FIG. 3. The axial direction is shown by arrow A, while the radial direction is shown by arrow R.

Figure 4A:
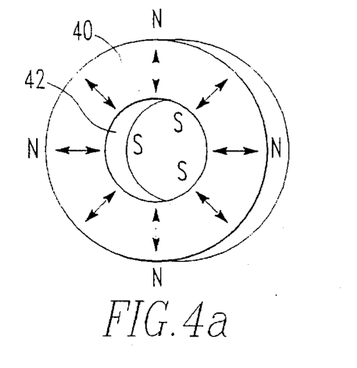
FIGS. 4a–4e are schematic representations showing fabrication of ring magnets to form cylindrical magnetic sections with angled ridges.
Figure 4B:
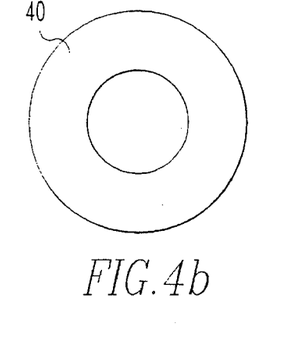
Figure 4C:
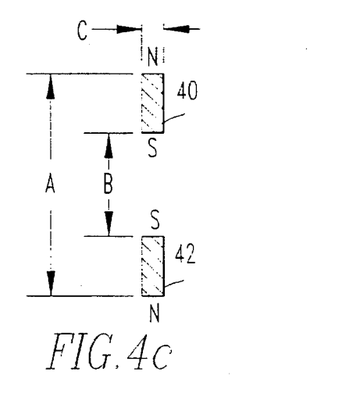
Figure 4D:
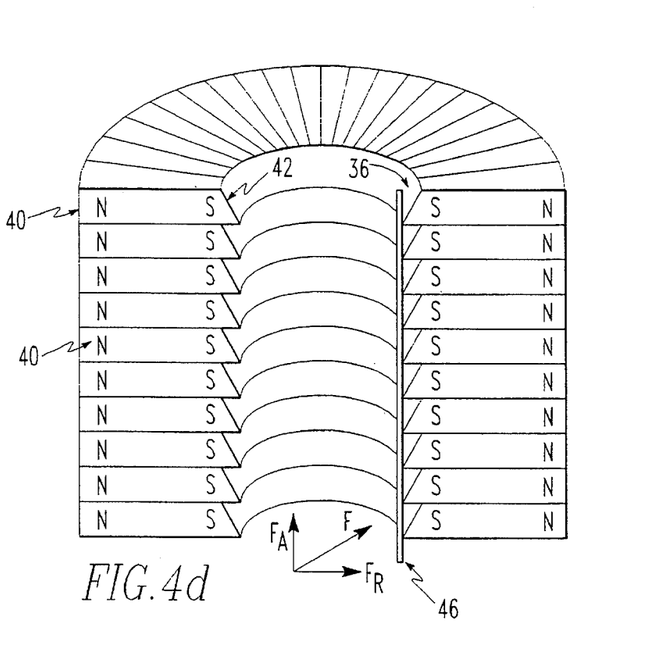
Figure 4E:
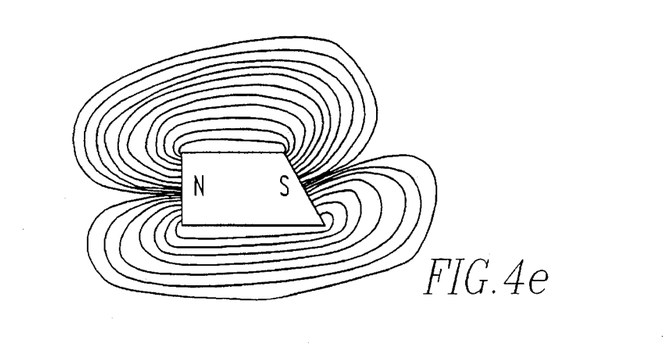

To accomplish this magnetic angle, α, the inner surface of the first magnetic section 22 and the second magnetic section 24 have ridged edges 32 to provide a flat surface 34 perpendicular to the desired angle of magnetization, α, as shown in FIG. 3. This is necessary due to the fact that magnetic flux lines always leave and enter the surfaces of ferromagnetic materials at right angles, as shown in FIG. 4e.

This angled magnetic configuration creates repulsive forces oriented both radially and axially. The radial component serves to maintain piston 12 alignment within the cylinder 16. The axial component provides the force required to return the piston 12 to the loaded position between contractions.

The magnitude of these forces is a function of magnetic field strength, field orientation and magnet separation. Preferably, the radial force vector, $F_R$ in FIG. 4d, is made as large as possible since it does not hinder axial motion. The axial force vector, $F_A$, must be small enough to allow muscle shortening against the afterload, yet be large enough to quickly return the muscle to its original length.

The ridged edges 32 of each magnetic section 22 and 24 are preferably filled with a non-magnetic material 36 to form a smooth outer surface. This is to prevent chipping should the piston 12 and cylinder 16 come in contact and also provides a better surface for the rolling diaphragms, 28 and 30, to conform to.

In order to form the ridged edges 32 efficiently, they can be formed using the following steps using stacked ring magnets 40, as shown in FIG. 4:

1. Start with a radially-magnetized ring washer 40 of NdFeB or SmCo, as shown in FIGS. 4a–4c where, for example, A is 2.5 cm, B is 1.5 cm and C is 0.1 cm.

2. Machine the inner surface 42 of the ring 40 to some angle $\alpha$ (e.g. 15°).

3. Stack a number of these rings 40 to form a cylinder as shown in FIG. 4d, where $F_R$ is the radial force vector, $F_A$ is the axial force vector and F is the total force vector. The magnetic field is directed so that the majority of force is directed radially and a smaller component is directed axially (for $\alpha=15°$, $F_R=F\cos 15°=0.96F$ and $F_A=F\sin 15°=0.25F$).

4. Fill ridged edges 32 with non-magnetic material 36 to protect from chipping (without reducing the inner diameter).

5. Coat the entire surface with a thin layer of non-magnetic material 46 (e.g. aluminum) to strengthen and stabilize the structure.

6. Repeat steps 1–5 with smaller rings 40 to make the first magnetic section 22 for the piston 12, (with the exception that the outermost surface is machined to some angle—not necessarily equal to $\alpha$).

By starting with radially-magnetized rings 40, which is a common configuration used by manufacturers, cylindrical magnetic sections 22 and 24 can be easily assembled by simple machining and stacking techniques. The resulting magnetic field can be manipulated by taking advantage of the fact that magnetic lines of force exit and enter ferromagnetic materials at right angles. The direction of the magnetic fields depends upon the angle at which the rings are machined, as shown in FIG. 4e.

The dynamic characteristics of the piston/cylinder system can be altered by changing the angle, $\alpha$, of machining the rings 40, the outer diameter A, inner diameter B and thickness, C, of the rings 40, the magnetic materials employed, or the axial distribution of the rings 40.

Figure 5:
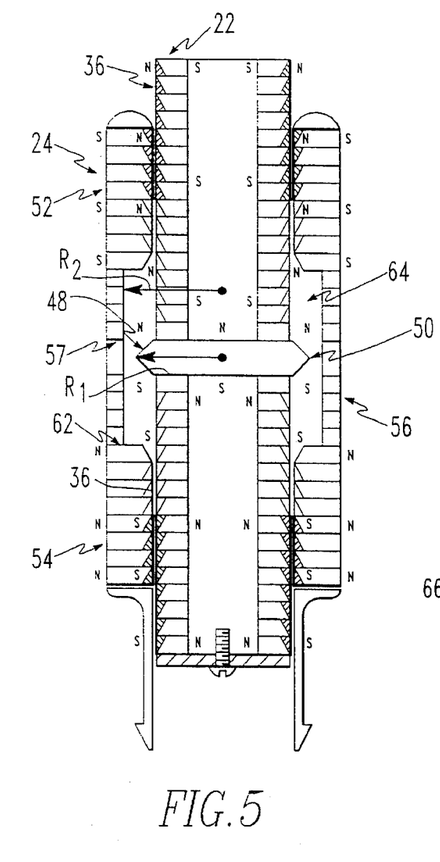
FIG. 5 is a schematic representation showing an embodiment of the muscle energy converter having a stroke regulation mechanism.

Should the piston 12 be allowed to move freely along its long axis, the rolling diaphragms 28, 30, could completely unroll and possibly bind the system. To eliminate this problem, an internal stroke regulator mechanism 48 is disclosed. The mechanism 48, as shown in FIG. 5, preferably comprises a central disc magnet 50 having a radius, $R_1$, slightly larger than an internal radius, $R_2$, of two separated portions 52, 54 of the second magnetic section 24 of the cylinder 16. The central disc 50 is positioned in the center of the piston 12. The second magnetic section 24 is divided into two portions 52, 54. There can be a two-piece spacer 56 between the two portions 52, 54. The central disc magnet 50 is magnetized so that, for example, its North pole faces the top of the device and its South pole is directed toward the I/O port 20. The magnets of the first portion 52 positioned at the top of the cylinder 16 have their North poles facing the piston/cylinder gap. This magnetic orientation is reversed for the magnets of the second portion 54 at the bottom of the cylinder 16. The length of the spacer 56 determines the distance the piston 12 is allowed to travel.

Figure 6:
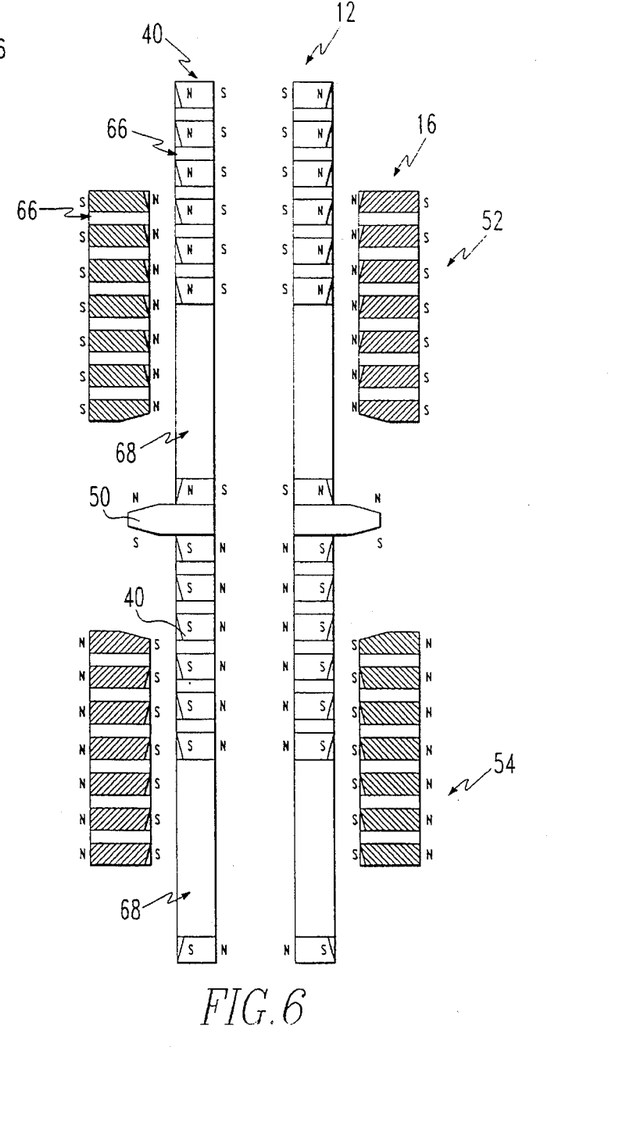
FIG. 6 is a schematic representation showing the muscle energy converter with spacers between the ring magnets to alter the magnetic dynamics.
Figure 7A:
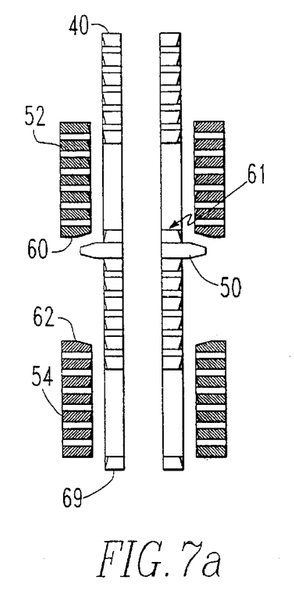
FIGS. 7a–7c are schematic representations showing the extension through compression cycles of the muscle energy converter.

As illustrated in FIG. 7a, as the piston 12 travels toward its preloaded position (extending out of the cylinder top), the North pole of the central disc magnet 50 is brought into close proximity to the North poles of the magnets of the first portion 52, slowing its motion. When the disc 50 closes to within 1 mm of the bottom-most magnet of portion 52, the repulsive forces and passive muscle tension will balance the axial preload forces and the piston 12 will stop. The bottom ring magnet 60 of first portion 52 is machined so that its North pole is directed against the central disc magnet opposite the direction of the other magnets in the first portion bearing stack 52, as shown in FIG. 6.

Figure 7B:
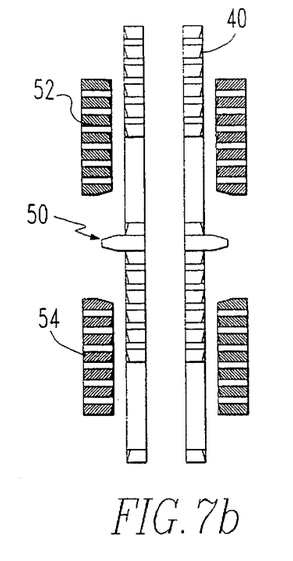
Figure 7C:
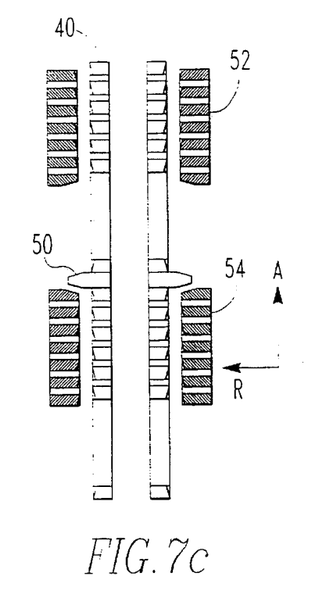

During compression (muscular contraction), as shown in FIG. 7c, the South pole of the central disc magnet 50 is brought into close proximity to the South poles of the bearing magnets of the second portion 54, again slowing its motion. When the disc 50 comes within ⁻1 mm of the upper-most bearing magnet 62 of the second portion 54, the repulsive forces will combine with the axial bearing forces to balance the compression force of the muscle and stop the piston 12. The ring magnet 62 on top of the second portion is machined so that its South pole is directed against the like pole of the central disc magnet 50 the same direction as the other magnets on the stack.

Figures 9, 10:
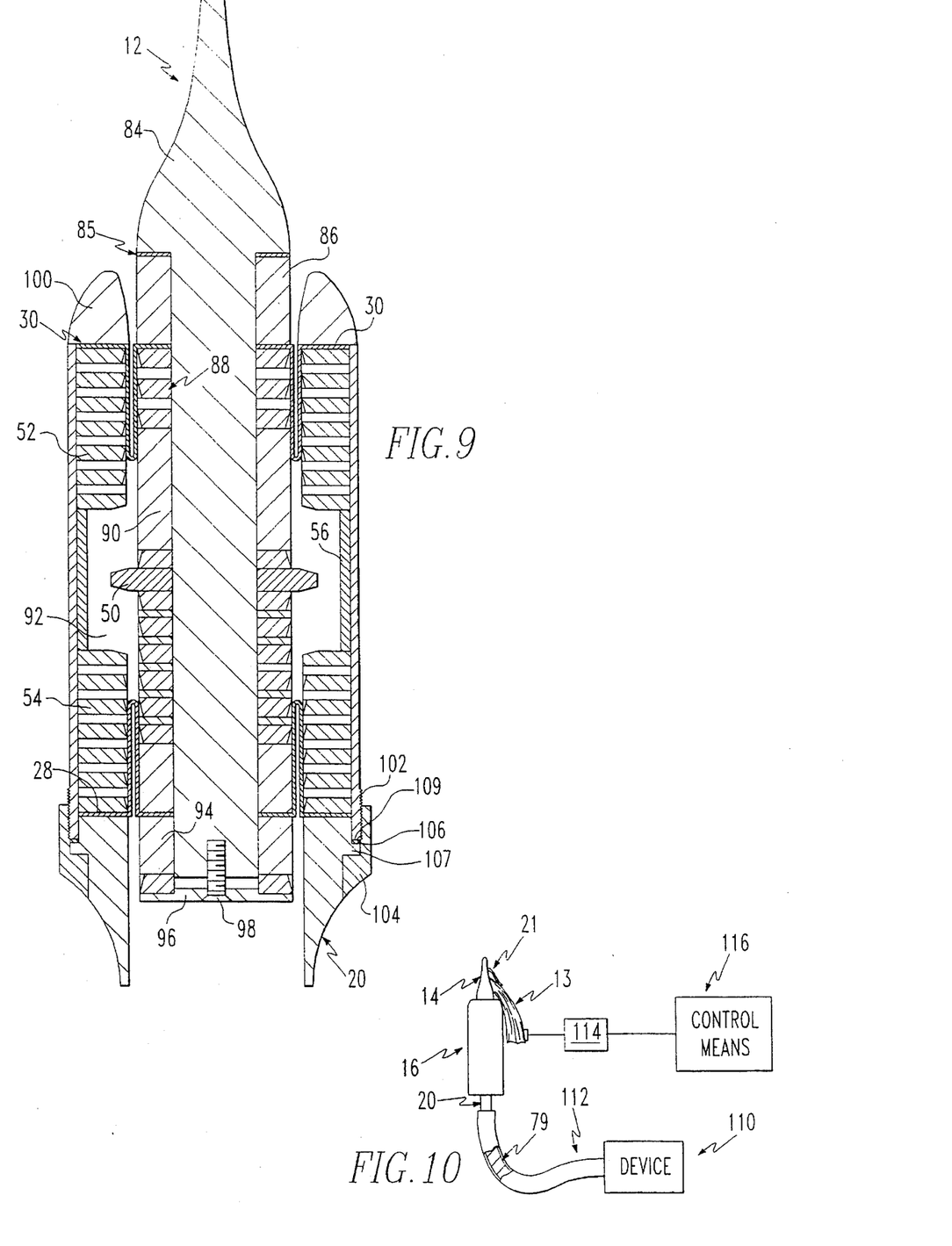
FIG. 9 is a schematic representation showing a preferred embodiment of the muscle energy converter.
FIG. 10 is a schematic representation showing the muscle energy converter in a complete system to power a device.

This construction shown in FIGS. 5 and 9 provides axial stabilization with no contacting surfaces and a simple means to assemble and disassemble the device. This construction also maintains radial stabilization at the top and bottom where it is needed the most and separates the rolling diaphragms 28 and 30 to further enhance radial stability. This design also provides access to the inside of the device to allow examination of its parts or introduction of internal bearing fluid (if necessary). It has been discovered that stacking of ring magnets reduces the field throughout the central portion 64 of the first magnetic section 22 of the piston 12. This phenomenon is presumed to be caused by the opposing magnetic forces generated from neighboring magnets in the stack. Juxtaposition of opposing magnets can reduce the alignment of magnetic domains within individual neodymium/iron rings, thereby reducing its overall magnetization. The magnets of the central portion 64, weakened by their neighbors, are more susceptible to being overpowered by the field of the first and second portions 52, 54 of the cylinder 16. The presence of piston magnets above and below the cylinder stack, as shown in FIG. 5, produce opposing axial forces that reduce the preload of the device. In fact, it has been discovered the total axial preload force reverses direction when the weakened central rings of the first magnetic sections 22 approach the top of the cylinder stack and the stronger end magnets approach the bottom.

As shown in FIG. 6, in order to minimize the demagnetization effects imposed on the stacked rings, spacers 66 can be introduced into the bearing design. Preferably, each spacer 66 will serve to separate the magnetic rings a desired distance and have a relative permeability of roughly 1.0. A low permeance is preferred to direct the lines of force into the piston/cylinder gap 68 before returning to their opposite pole, thereby maximizing the repulsion between piston 12 and cylinder 16.

Selected sections of the piston 12 can be replaced with non-magnetic segments 68 to eliminate forces which counteract the preload needed to extend the piston 12. This embodiment does not seriously impair lateral bearing forces because the remaining magnets still provide significant support throughout the pump cycle.

Note that, as shown in FIG. 7a, the central magnetic disk 50 combines with its neighboring magnet above 61 and the ring magnet 69 stationed at the bottom of the piston 12 to balance the preload forces present at the top of the stroke (full extension). At full compression, FIG. 7c, the magnetic disc 50 is repulsed to add preload force and counteract the force of the muscle.

Preferably, magnets are made from Cookson's Bremag (bonded neodymium iron boron) and can be readily machined to the configuration. The specific ring magnets depicted are as follows:

Modified Cylinder magnets #NB048A manufactured by Dexter Magnetics, Inc.:

A: 1.81"

B: 0.0710"

C: 0.079"

Piston magnets #NB047C

A: 0.598:

B: 0.335"

C: 0.098

Cylinder gap (equal to the separation of segments 52 and 54): 0.866" (2.2 cm)

Diaphragm: 4-71(60)70-BBJ-1 manufactured by Bellofram Corp.

(maximum stroke length=0.98" (2.49 cm))

Figure 7D:
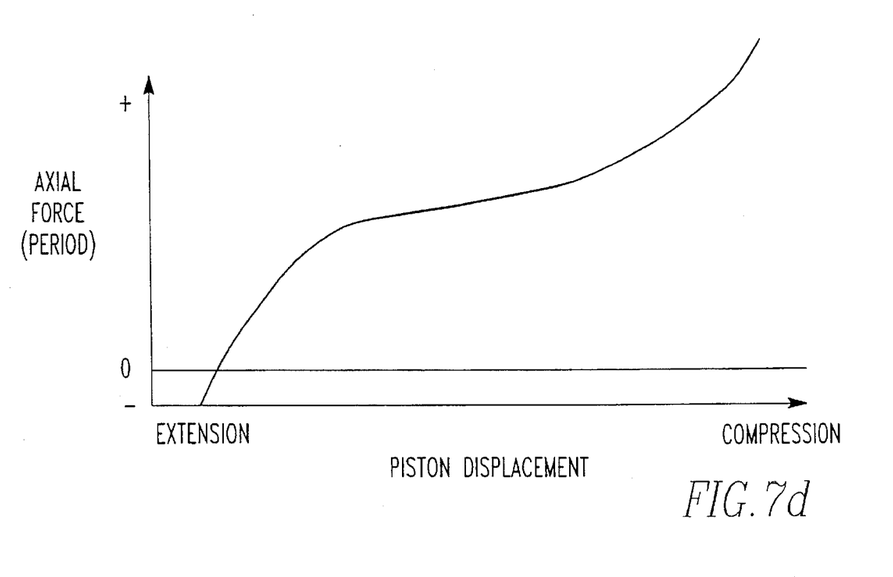
FIG. 7d is a graph showing axial preload force vs. piston displacement of the muscle energy converter.

The spacer design alters the force/displacement curve to approximate the graph shown in FIG. 7d. At full extension, (FIG. 7a), the "braking" forces of the central disc 50 and second portion ring magnets counter-balance the preload forces (resulting in zero total axial force). As the piston 12 moves into the chamber 18 (FIG. 7b), the braking force rapidly decreases and the preload force intensifies as more magnets come into close proximity (some rippling may occur due to the "lumpy" field produced by the magnet stacks).

Near full compression, as shown in FIG. 7c, maximum axial forces (due to magnet overlap) combine with disc 50 braking forces to produce a large preload force that stops the piston 12 and ultimately reverses its direction. The disc 50 braking forces act over a short distance and come into play only at the extremes of the piston stroke.

The present invention is also a method of using muscle energy. The method comprises the steps of attaching a muscle to an attachment head of a piston so that the muscle can move the piston within a cylinder to pressurize fluid within the cylinder. Then there is the step of maintaining frictionless alignment of the piston within the cylinder with opposing magnetic fields produced by first and second magnetic sections in the piston and cylinder, respectively. Preferably, there is the step of producing with the first and second magnetic sections a preload force on the piston. Preferably, after the attaching step, there is the step of using the fluid to perform work with the human body such as to pump blood.

Figure 8:
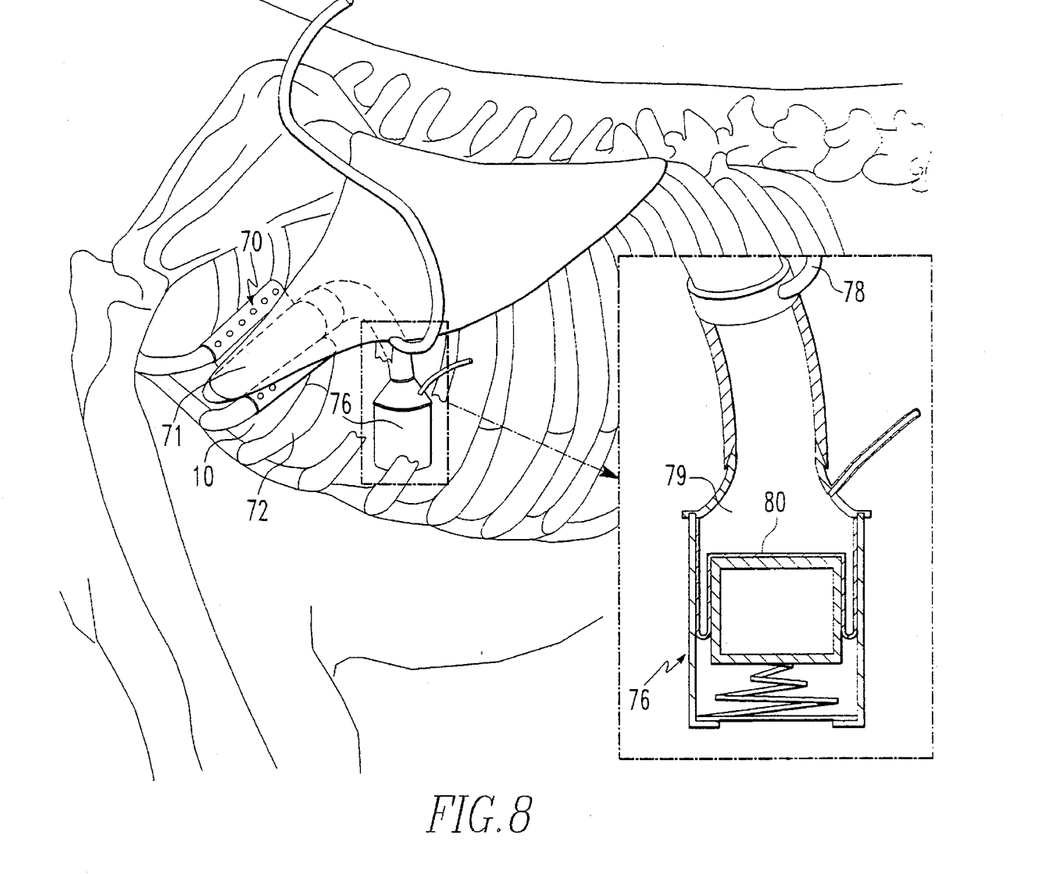
FIG. 8 is a schematic representation showing the muscle energy converter implanted in a canine for experimentation.

In order to test the invention, it can be implanted in a dog as shown in FIG. 8 which shows a proposed experimental arrangement. The cylinder 16 is attached between the ribs 72 with rib support brackets 70. The head 14 is attached to the latissimus dorsi muscle 71. Hydraulic fluid is moved and pressurized by movement of the muscle. The fluid 79 flows into an implanted afterload device 76 and is measured with flow probe 78. Rolling diaphragm 80 seals the afterload device 76. Infusion port 82 is provided for transference of hydraulic fluid 79.

In a preferred embodiment of the inventions, as shown in FIG. 9, the piston 12 is comprised of a piston shaft 84 which extends through the cylinder 16. Disposed about the shaft 84 is a polyurethane washer 85 and an upper magnetic piston stack 86, then an end (flange) of rolling diaphragm 30, followed by an upper portion 88 of the piston magnetic section 22 and then a central nonmagnetic piston stack 90. A lower portion 92 of the piston's magnetic section having the central ring magnet 50 is disposed about the piston shaft 84 followed by a lower magnetic piston stack 94. The entire piston assembly is held stacked together with a piston clamp plate 96 and a piston clamp bolt 98.

The cylinder 16 is comprised of a cylinder housing 100, a first magnetic portion 52, a one-piece spacer cylinder 56 and a second magnetic portion 54. The port 20 is connected to a threaded end 102 of the cylinder housing 100 with a threaded collet 104. An O-ring 106 is disposed between the cylinder housing 100 and the port 20. In order to fluidically seal the piston 12 to the cylinder 16 in a frictionless manner, first and second rolling diaphragms 28 and 30 are used.

The assembly of the muscle energy converter 10 as shown in FIG. 9 can be as follows:

1. slide polyurethane washer 85 against the underside of head 14 of the piston shaft/head assembly 84;

2. slide upper piston stack 86 against washer 85 and piston shaft/head assembly 84 noting proper magnet orientation;

3. place upper rolling diaphragm 30 inside the cylinder housing 100 so that its flange covers the inner ceiling of the housing 100 (rolling diaphragm not convoluted);

4. slide upper cylinder stack 52 into the cylinder housing 100 so that it compresses the upper rolling diaphragm flange 30 against the housing 100 noting proper magnet orientation;

5. slide spacer cylinder 56 into the cylinder housing 100 so that it rests against the upper cylinder stack 52;

6. slide piston shaft/head assembly 84 with washer 85 and upper piston stack through the opening of the upper rolling diaphragm 30 so that the upper piston stack 86 rests within the side walls of the upper rolling diaphragm 30;

7. slide the central piston stack 90 onto the piston shaft assembly 84 until it compresses the upper rolling diaphragm 30 against the upper piston stack 86 noting proper magnet orientation;

8. move the partially-assembled piston 12 toward the top of the cylinder housing 100 so that the upper rolling diaphragm 30 forms a convolution (i.e. folds over on itself);

9. slide the lower cylinder stack 54 into the cylinder housing 100 so that it rests against the spacer cylinder 56 noting proper magnet orientation;

10. place the convoluted lower rolling diaphragm 28 over the piston shaft assembly 84 so that its sidewalls are completely supported by the central piston stack 90 and the lower cylinder stack 54;

11. slide the lower piston stack 94 onto the piston shaft assembly 84 until it compresses the lower rolling diaphragm 28 against the central piston stack 90 noting proper magnet orientation;

12. center the piston clamp plate 96 against the bottom of the lower piston stack 94;

13. thread the piston clamp bolt 98 through the recessed central aperture of the piston clamp plate 96 and into the threaded piston shaft assembly 84;
14. tighten the piston clamp bolt 98 so that all piston components are pressed tightly together and both rolling diaphragm heads are held securely between the piston stacks 86, 90, 94;
15. place the O-ring 106 in the upper ridge 107 of the outlet port 20;
16. place the inlet/outlet port 20 against the flange of the lower rolling diaphragm 28 so that the O-ring 106 opposes the lower rim 109 of the cylinder housing 100;
17. place the threaded collet 104 over the inlet/outlet port 20 and secure to the cylinder housing 100 by screwing the collet 104 onto the threads of the cylinder housing 100; and
18. tighten the threaded collet 104 so that the internal cylinder components 52, 54 and 56 are compressed between the cylinder housing (100) and inlet/outlet port 20 and both rolling diaphragm flanges 28, 30 are held securely between the cylinder stacks and housings 100, 20.

Preferably, the components are machined from non-magnetic materials (e.g. aluminum, titanium, 300-series stainless steel, plastic, etc.) Materials of varying permeability may be chosen for specific components as a means of manipulating the magnetic field.

A complete system using the muscle energy converter 10 is shown in FIG. 10. The muscle 13 is stimulated using a stimulator 114 controlled by control means 116. Several different implantable pulse-train generators (IPGs) can be employed to stimulate and condition skeletal muscle for powering the muscle energy converter 10. The Itrel 7420 (Medtronic) neurostimulator is an implantable pulse-train generator that has been used in a variety of muscle training protocols. However, it cannot be synchronized with the heart, and therefore is not suitable for experiments using muscle for ventricular assistance. Many studies have utilized the expanded capabilities of the Medtronic SP1005 cardiomyostimulator, which can generate a wide variety of pulse trains in synchrony with the heart or as infrequently as every fourth beat. Two other cardio-synchronous muscle pacers are also frequently utilized: the Prometheus IPG (Medtronic) and the Telectronics CSM. Both offer a wide range of stimulation variables, thereby permitting various training and pacing regimens. These variables include: synchronization ratio (as low as every tenth beat); burst duration; pulse interval; pulse width; burst delay; and pulse amplitude. In addition, the Prometheus IPG has the unique ability to automatically adjust burst duration and delay as a percentage of the sensed cardiac cycle.

Unlike cardiac muscle, skeletal muscle does not behave as an electrical syncytium. Therefore, coordinated contraction is most efficiently achieved through stimulation of the motor nerve. In testing, seven canine latissimus dorsi muscles (LDM) were used to evaluate the effects of electrode position and stimulation profile on contractile response. Two types of perineural (PN) bipolar leads were placed on the thoracodorsal nerve near its junction with the LDM. Four unipolar intramuscular (IM) electrodes were woven transversely across the LDM. The first was placed at the most proximal bifurcation of the nerve, while the other three equally divided the LDM into thirds. Peak isometric contractile force was measured during single and burst stimulations ranging from 0.1 to 10.0 volts. Each pulse train consisted of six pulses delivered at a frequency of 30 Hz.

The threshold voltage (minimum voltage required to produce measurable tension), plateau voltage (minimum voltage necessary for maximum force generation), and maximum force were measured and are summarized in Table 1. Perineural leads resulted in significantly lower threshold and plateau voltages than did any IM electrode pair in both single and burst stimulation modes. Threshold and plateau voltages progressively rose as the distance from the neurovascular pedicle to the IM electrode pairs was increased. As compared to a single stimulus, burst stimuli achieved a significantly higher maximal force, no matter which electrodes were used.

TABLE 1

Stimulation/Contraction Parameters of Perineural and Intramuscular Leads

| Lead Type | Stimulation Mode | Threshold Voltage | Plateau Voltage | Max. Force (Newtons) |
| --- | --- | --- | --- | --- |
| 360° Perineural | Burst | $0.2 \pm 0.04$ | $0.7 \pm 0.06$ | $37 \pm 3$ |
| 180° Perineural | Burst | $0.4 \pm 0.1$ | $1.0 \pm 0.2$ | $38 \pm 4$ |
| IM Proximal | Burst | $1.7 \pm 0.2$ | $4.7 \pm 0.7$ | $35 \pm 5$ |
| IM Middle | Burst | $3.5 \pm 0.3$ | $9.7 \pm 0.1$ | $26 \pm 5$ |
| IM Distal | Burst | $4.1 \pm 0.6$ | $9.6 \pm 0.2$ | $15 \pm 4$ |
| All | Burst | $1.9 \pm 0.2$ | $5.3 \pm 0.5$ | $32 \pm 2$ |
| All | Single | $2.1 \pm 0.2$ | $4.7 \pm 0.4$ | $9.8 \pm 4$ |

Results expressed as mean = SEM

This study (Furnary, A., Trumble, D., Vu, T., Magovern, G., and Kao, R. Perineural leads and burst stimulation optimize contraction of skeletal muscle. ASAIO Transactions, vol. 37, 164–166, 1991) clearly demonstrates that PN leads are more efficient for muscular excitation. Moreover, these leads have been used in chronic studies for up to one year without detrimental effects on the motor nerve. Burst stimulation elicits greater maximal force than a single pulse and does so independent of electrode type.

In an isometric endurance study (Kao, R., Trumble, D., Magovern, G. Fatigue resistance muscle with preserved force and mass for cardiac assist. J. Cardiac Surgery, vol. 6, 210–217, 1991), six sheep under general anesthesia had their left and right LD muscles mobilized for perineural electrode and pulse generator implantation. Each muscle was encased in surgical membrane to avoid tissue adhesions and revascularization. After a 10-day recovery period, the left side muscles were paced at a gradually increasing rate (30–120 pulse-trains/min) over a three-month period. Each burst stimulus consisted of six pulses delivered at 30 Hz over a 190-msec time interval. At four months after operation, the tendinous end of each LD muscle was freed from its humeral insertion and attached to a strain gauge transducer for isometric force measurements. Both left and right muscles from each animal were stimulated to contract for 2 hours before being isolated, trimmed, and weighted. Frozen tissue biopsies were used to determine creatine phosphate, adenosine triphosphate (ATP), lactate, and glycogen content as well as myosin ATPase and succinate dehydrogenase (SDH) activities.

The arterial diameter in the conditioned muscle was 30% larger than that of the control muscle and had a 40% higher blood flow at rest. A three- to five-fold increase in blood flow during the endurance test was observed. A steady-rate isometric force of 3.05N was achieved in the conditioned muscle versus 0.79N for the control group. The mass and cross-sectional areas of conditioned and unconditioned muscles were similar. Electric conditioning increased fatigue-resistant fiber content from 33% to 92%, as evidenced by myosin ATPase activity. During the early phases of the fatigue test, a lower lactate production was found for the conditioned muscles, indicating the increased oxidative capacity of the transformed muscle. This was also confirmed by the higher oxygen uptake and SDH activity. This study indicates that it is possible to produce fatigue-resistant muscle with preserved muscle mass and significant contractile strength.

Isometric testing measures muscular strength, but work production and contractile speed cannot be determined because the muscle is not allowed to shorten. To eliminate this problem, a muscle-actuated piston pump (MAPP) was designed and constructed. (Trumble, D., Kao, R., Magovern, G. Quantification of skeletal muscle work capacity for circulatory assistance. Cardiovascular Sci. & Tech.: Basic and Applied II, 388–389, 1991.) This device quantifies the amount of external work extracted from paced muscle by efficiently converting energy into the hydrodynamic pressures and flows of a Penn State mock circulatory system.

The muscle is attached to the MAPP by a thin cable which traverses a stationary pulley and is fixed to one end of a lever. Attached to the opposite end of the lever is a piston mounted on a rolling diaphragm. As the muscle contracts, it pulls up on one end of the lever, forcing the piston down an equal distance. Beneath the piston lies a fluid-filled chamber with a tilting-disc valve placed at each end to provide uni-directional flow. Pressures are measured within the pump chamber and in the systemic and venous compliance chambers of the mock loop. Flow is measured using an ultrasonic flowprobe positioned at the outlet port of the MAPP. Bench tests have shown no discernible energy losses within the MAPP system. This is due primarily to the frictionless nature of the rolling diaphragm which supports the piston head. As a result, the energy produced by the muscular contraction may be measured directly in the form of pressures and flows.

Six canine LD muscles were evaluated using the MAPP/mock loop system. The muscles were not mobilized, thereby preserving their collateral circulation. A customized stimulating lead was implanted over the thoracodorsal nerve. The tendinous insertion of the LD to the humerus was transected and connected to the MAPP. Preload was adjusted to return the LD to its in-situ length, and pulse trains were delivered at a rate of 60 per minute. Each burst stimulus consisted of 11 pulses delivered at a rate of 43 Hz. Under these conditions, average peak power levels reached 10.75 watts, while mean power during shortening exceeded 5.5 watts. This level of performance easily exceeds that of many previous studies, and reflects the improved muscle perfusion that results when the LD is left in situ and not mobilized from the chest wall on a single vascular pedicle. These data are especially encouraging since the average mass of these muscles was only 200 grams.

A typical left ventricle (350 g) must deliver approximately 3.3 watts during systole to move 5.0 L/min against a pressure gradient of 100 mmHg. These canine LD muscles generated 38% more energy with 43% less mass. These results imply that large skeletal muscle (>450 g) could generate enough mechanical work to support the entire circulation (even if the conditioning process weakens the muscle by as much as 50%).

As shown in FIG. 10, the muscle energy converter 10 may be used to power a variety of devices 110 including:

a) intra-aortic balloon pumps wherein the muscle tendon 21 is attached to the head 14 of the muscle energy converter 10 and contraction pulls the piston 12 into the cylinder 16 thereby displacing fluid under pressure through the outlet port 20. The outlet port 20 communicates with the intra-aortic balloon pump 110 through a non-compliant conduit 112 filled with incompressible fluid so that the volume displaced from the converter 10 pushes a similar volume of fluid into the balloon pump 110 without delay. This pressurized fluid 79 may fill the balloon directly or activate a second piston which translates low-volume, high pressure hydraulics to a higher volume, lower pressure displacement more suitable for aortic counterpulsation. Muscle contraction is activated by a cardio-myostimulator 114 that monitors the heart and sends a burst of stimuli to the muscle so that contraction coincides with the diastolic phase of the cardiac cycle. In this way, fluid 79 inflates the balloon within the walls of the aorta and displaces blood such that cardiac afterload is reduced and coronary perfusion is increased. Following contraction, the balloon is deflated as the piston 12 is pushed from the cylinder 16 by the described axial preload magnetic forces and fluid 79 is drawn back towards the muscle energy converter 10.

b) extra-aortic counterpulsation pumps activated in the same manner as a) with the exception that the aorta is compressed from the outside via balloon inflation or pusher-plate actuation. This scheme employs no blood-contacting components, thereby avoiding complications due to thrombosis, hemolysis and balloon calcification. A balloon occluder device is disclosed in U.S. patent application Ser. No. 08/228,150, titled "Occluder Device and Method of Making", by John J. Pacella and Richard E. Clark, having attorney docket number AHS-3, filed the same day as the present application.

c) intra-ventricular balloon pumps activated in the same manner as a) with the exception that the balloon is placed within the ventricular cavity of the heart and inflated during the systolic portion of the cardiac cycle to increase cardiac output and reduce the work required of the native heart.

d) cardiac compression devices activated in the same manner as a) with the exception that the pressurized fluid 79 activates a hydraulic mechanism 110 external to the heart (e.g. pusher-plates, balloon patches, etc.) so that the ventricle(s) of the heart are compressed through direct displacement of the epicardium during the systolic portion of the cardiac cycle to increase cardiac output and reduce the work required of the native heart. This scheme employs no blood-contacting components, thereby avoiding complications due to thrombosis, hemolysis and balloon calcification.

e) positive displacement ventricular assist devices (left or right) activated in the same manner as a) with the exception that the pressurized fluid displaces a pusher-plate that in turn compresses a flexible blood-filled sack and expels blood from the pump during the systolic portion of the cardiac cycle.

f) positive displacement bi-ventricular assist devices and total artificial hearts—identical to e) with the exception that two blood pumps are activated simultaneously.

This invention may also be used in an assortment of other noncardiac applications such as:

g) actuation of hydraulic balloon occluder devices employing the same hydraulic actuation method described in a) with the exception that the device 110 inflates around some vessel or prosthetic conduit such that the lumen is collapsed and flow is restricted. Muscle contraction is activated with a myostimulator 114 triggered automatically by some event (e.g. motor failure of an implanted centrifugal pump) or manually by placing a magnet over the myostimulator 114 (e.g. for use as an artificial sphincter).

h) voluntary muscular actuation of prosthetic limbs employing the same hydraulic actuation method described in a) with the exception that the target device 110 comprises a hydraulic piston connected across the joint of a prosthetic limb (e.g. artificial elbow, hand, knee, etc.). In this manner, the limb is activated by the voluntary contraction and relaxation of the muscle attached to the muscle energy converter 10.

i) hydraulic displacement of the diaphragm (or some replacement prosthesis) to aid in respiration employing the same hydraulic actuation method described in a) with the exception that the target device 110 (e.g. a piston) displaces the diaphragm (or replacement prosthesis) downward so that intrathoracic pressure is reduced and inspiration ensues. Expiration may also be aided by the active removal of fluid from the diaphragm piston by the magnetic bearing of the muscle energy converter 10. Muscle contraction and subsequent muscle energy converter compression is activated by a myostimulator 114 which can be triggered by impulses received from the phrenic nerve or pre-programmed in a control means 116 to deliver burst stimuli at a certain rate.

j) augmentation of lymphatic flow via hydraulic compression of large lymphatic vessels employing the same hydraulic actuation method described in a) with the exception that the target device 110 (e.g. a fluid-filled balloon) periodically squeezes a major lymphatic duct such that its contents are expelled, thereby increasing lymphatic flow. Muscle contraction and subsequent muscle energy converter 10 compression can be activated by a myostimulator 114 pre-programmed to deliver burst stimuli at a certain rate by control means 116.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A muscle energy converter comprising:
   a piston having an attachment head for connection to a muscle, said piston having material which is magnetically reactive; and
   a cylinder having a chamber in which the piston is disposed, said cylinder having a port connected to the chamber for transport of fluid in the chamber as the muscle moves the piston, said piston comprising a first magnetic section having at least one magnet and said cylinder comprising a second magnetic section having at least one magnet, said first magnetic section and said second magnetic section providing opposing fields to maintain the piston in co-axial alignment within the cylinder.

2. A muscle energy converter as described in claim 1 wherein the first and second magnetic sections provide opposing fields to maintain the piston in co-axial alignment and essentially out of contact with the cylinder so movement of the piston within the cylinder is essentially frictionless.

3. A muscle energy converter as described in claim 2 including a rolling diaphragm sealing mechanism connected between the piston and the cylinder.

4. A muscle energy converter as described in claim 3 wherein the rolling diaphragm mechanism comprises a first rolling diaphragm and a second rolling diaphragm in spaced relationship with said first rolling diaphragm.

5. A muscle energy converter as described in claim 4 wherein the cylinder has an axis having an axial direction associated with it and a radius having a radial direction associated with it perpendicular to its axial direction and the piston moves relative to the cylinder in the axial direction perpendicular to the radial direction, said opposing fields of the first magnetic section and the second magnetic section disposed at an angle between the axial and radial directions so that the piston is subject to a radial aligning force and an axial preload force.

6. A muscle energy converter as described in claim 5 wherein the first magnetic section and the second magnetic section comprise a series of ridged edges forming flat surfaces from which the opposing magnetic fields are emitted at an angle between the axial and radial directions.

7. A muscle energy converter as described in claim 6 wherein the first and second magnetic sections comprise a nonmagnetic cover material disposed over the ridged edges to form a smooth outer surface.

8. A muscle energy converter as described in claim 7 wherein the attachment head comprises at least one channel through which an end of the muscle can be disposed therethrough for attachment.

9. A muscle energy converter as described in claim 8 wherein the movement of the piston along the cylinder defines a stroke, and including a stroke regulation mechanism.

10. A muscle energy converter as described in claim 9 wherein the second magnetic section includes a first portion and a second portion with a space therebetween the stroke regulation mechanism comprises a central ring magnet fixedly connected to the piston which opposes the first portion and a second portion of the second magnetic section, said ring magnet disposed in the space between the first and second portions for providing travel.

11. A muscle energy converter as described in claim 1 wherein the cylinder comprises means for a stable attachment within a body.

12. A muscle energy converter as described in claim 11 wherein the first and second magnetic sections are comprised of a series of stacked ring magnets, each of said ring magnets having a beveled edge corresponding to the angle.

13. A muscle energy converter as described in claim 12 wherein the first and second magnetic sections comprise nonmagnetic stacked ring spacers disposed between some of the ring magnets.

14. A method of using muscle energy comprising the steps of:
    attaching a muscle to an attachment head of a piston so that the muscle can move the piston within a surrounding cylinder to pressurize fluid within the cylinder to perform work within the human body;
    securing the cylinder in a stable attachment with a body with the muscle: and
    maintaining frictionless alignment of the piston within the cylinder with opposing magnetic fields produced by first and second magnetic sections in the piston and cylinder, respectively.

15. A method as described in claim 14 including the step of producing, with the first and second magnetic sections, a preload force on the piston.

16. A method as described in claim 15 wherein the attachment head includes a slot and the attaching step includes the steps of threading a tendon of the muscle through a slot in the attachment head and suturing the tendon back onto itself.

17. A method as described in claim 15 wherein after the attaching step, there is the step of using the fluid to perform work within the human body.

* * * * *